United States Patent
Ullah et al.

(10) Patent No.: US 7,122,207 B2
(45) Date of Patent: Oct. 17, 2006

(54) HIGH DRUG LOAD ACID LABILE PHARMACEUTICAL COMPOSITION

(75) Inventors: Ismat Ullah, Cranbury, NJ (US); Gary J Wiley, Jackson, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 446 days.

(21) Appl. No.: 09/848,448

(22) Filed: May 3, 2001

(65) Prior Publication Data

US 2001/0051188 A1    Dec. 13, 2001

Related U.S. Application Data

(63) Continuation-in-part of application No. 09/735,059, filed on Dec. 12, 2000, now abandoned, which is a continuation of application No. 09/408,098, filed on Sep. 29, 1999, now Pat. No. 6,224,910, which is a continuation of application No. 09/083,579, filed on May 22, 1998, now abandoned.

(51) Int. Cl.
*A61K 9/16*    (2006.01)
*A61K 9/48*    (2006.01)
*A61K 9/52*    (2006.01)
*A61K 9/54*    (2006.01)
*A61K 9/60*    (2006.01)

(52) U.S. Cl. .................. 424/490; 424/451; 424/452; 424/457; 424/458; 424/459; 424/461

(58) Field of Classification Search ............... 424/451, 424/489, 490, 491, 452, 457, 458, 459, 461, 424/462, 493, 494
See application file for complete search history.

(56) References Cited

U.S. PATENT DOCUMENTS

| | | | |
|---|---|---|---|
| 4,432,966 A | 2/1984 | Zeitoun et al. ............... 424/21 |
| 4,524,060 A | 6/1985 | Mughal et al. ............... 424/19 |
| 4,556,552 A | 12/1985 | Porter et al. .................. 424/32 |
| 4,704,295 A | 11/1987 | Porter et al. .................... 424/3 |
| 4,728,512 A | 3/1988 | Mehta et al. ............... 424/458 |
| 4,775,536 A | 10/1988 | Patell ......................... 424/471 |
| 4,786,505 A | 11/1988 | Lovgren et al. ........... 424/468 |
| 4,794,001 A | 12/1988 | Mehta et al. ............... 424/458 |
| 4,808,413 A | 2/1989 | Joshi et al. ................. 424/458 |
| 4,853,230 A | 8/1989 | Lovgren et al. ........... 424/466 |
| 4,861,759 A | 8/1989 | Mitsuya et al. .............. 514/46 |
| 4,920,210 A * | 4/1990 | Koszalka et al. ............ 536/24 |
| 4,925,279 A | 5/1990 | Shirota ....................... 350/415 |
| 4,925,675 A | 5/1990 | Giannini et al. ........... 424/469 |
| 4,975,283 A | 12/1990 | Patell ......................... 424/470 |
| 4,994,279 A | 2/1991 | Aoki et al. ................. 424/494 |
| 5,026,559 A | 6/1991 | Eichel et al. ............... 424/458 |
| 5,026,560 A | 6/1991 | Makino et al. ............. 424/494 |
| 5,049,394 A * | 9/1991 | Howard et al. ............. 424/490 |
| 5,109,003 A * | 4/1992 | Tanaka et al. ......... 514/263.36 |
| 5,158,777 A | 10/1992 | Abramowitz et al. ....... 424/458 |
| 5,175,003 A | 12/1992 | Goldman .................... 424/484 |
| 5,225,202 A * | 7/1993 | Hodges et al. .............. 424/480 |
| 5,254,539 A * | 10/1993 | Mitsuya et al. ............... 514/46 |
| 5,326,570 A | 7/1994 | Rudnic et al. .............. 424/458 |
| 5,350,584 A | 9/1994 | McClelland et al. ........ 424/501 |
| 5,422,121 A | 6/1995 | Lehmann et al. ........... 424/464 |
| 5,510,114 A | 4/1996 | Borella et al. .............. 424/452 |
| 5,536,507 A | 7/1996 | Abramowitz ............... 424/479 |
| 5,556,839 A | 9/1996 | Greene et al. ................ 514/29 |
| 5,616,566 A | 4/1997 | Mitsuya et al. ............... 514/47 |
| 5,686,106 A | 11/1997 | Kelm et al. ................. 424/463 |
| 5,707,646 A * | 1/1998 | Yajima et al. .............. 424/439 |
| 5,725,886 A * | 3/1998 | Erkoboni et al. ........... 424/499 |
| 5,733,575 A | 3/1998 | Mehra et al. ............... 424/480 |
| 5,880,106 A | 3/1999 | Ullah et al. |
| 6,207,650 B1 * | 3/2001 | Bogardus et al. ............. 514/45 |
| 6,262,086 B1 | 7/2001 | Whittle et al. .............. 514/338 |
| 6,274,173 B1 * | 8/2001 | Sachs et al. ................ 424/480 |

FOREIGN PATENT DOCUMENTS

| | | |
|---|---|---|
| CA | 2016765 A | 11/1990 |
| EP | 0 287 536 A1 | 10/1988 |
| EP | 0 436 110 A1 | 11/1990 |
| EP | 0 255 404 B1 | 1/1991 |
| EP | 0 689 840 A1 | 6/1995 |
| EP | 0 754 452 | 1/1997 |
| EP | 0 781 549 | 7/1997 |
| EP | 1 079 809 | 12/2005 |
| WO | WO 88/02629 | 10/1987 |
| WO | WO 90/14091 A1 | 11/1990 |
| WO | 94/03160 * | 2/1994 |
| WO | WO 94/03160 | 2/1994 |

(Continued)

OTHER PUBLICATIONS

Ishibashi, et al., "Design and Evaluation of a New Capsule-Type Dosage Form for Colon-Targeted Delivery of Drugs", *Int'l. J. of Pharmaceutics*, 168 (1998) pp. 31-40.

*Primary Examiner*—S. Tran
(74) *Attorney, Agent, or Firm*—Burton Rodney

(57) ABSTRACT

A high drug load spheronized beadlet is provided wherein said beadlet comprises about 80% to 100% by weight of an acid labile medicament, preferably didanosine, about 0% to about 10% by weight of a disintegrant, and about 0% to about 10% by weight of a binder selected from the group consisting of sodium carboxymethylcellulose, hydroxypropylmethylcellulose, potassium alginate, and partially pregelatinized corn starch. A high drug load pharmaceutical composition, comprising the beadlet, with an enteric coating disposed thereon, is also provided.

23 Claims, No Drawings

| | FOREIGN PATENT DOCUMENTS | | WO | WO 9725066 A1 * | 7/1997 |
|---|---|---|---|---|---|
| WO | WO 97/25066 | 7/1997 | * cited by examiner | | |

HIGH DRUG LOAD ACID LABILE PHARMACEUTICAL COMPOSITION

RELATED APPLICATIONS

This application is a Continuation-in-Part of U.S. Ser. No. 09/735,059, filed Dec. 12, 2000, now abandoned, which is a continuation of U.S. Ser. No. 09/408,098, filed Sep. 29, 1999, now U.S. Pat. No. 6,224,910, which is a continuation of U.S. Ser. No. 09/083,579 filed on May 22, 1998, now abandoned, each of which is incorporated in its entirety, herein, by reference.

BACKGROUND OF THE INVENTION

2',3'-dideoxyinosine, which is also known as didanosine or ddI, is an acid labile drug which will degrade in the stomach. Didanosine has the following structural formula.

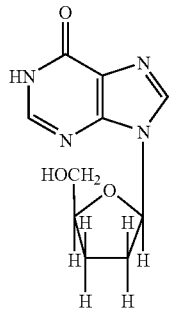

Didanosine is known to be effective in the treatment of patients with the HIV virus by inhibiting HIV replication. Furthermore, ddI has become widely used as a component of the therapeutic cocktails for treating AIDS.

Didanosine is generally available in a variety of oral dosages, including Chewable/Dispersible Buffered Tablets in strengths of 25, 50, 100 or 150 mg of didanosine. Each tablet is buffered with calcium carbonate and magnesium hydroxide. Didanosine tablets also contain aspartame, sorbitol, microcrystalline cellulose, Polyplasdone®, mandarin-orange flavors and magnesium stearate. Didanosine Buffered Powder for Oral Solution is supplied for oral administration in single-dose packets containing 100, 167 or 250 mg of didanosine. Packets of each product strength also contain a citrate-phosphate buffer (composed of dibasic sodium phosphate, sodium citrate, and citric acid) and sucrose. A didanosine Pediatric Powder for Oral Solution is also available and which is supplied for oral administration in 4- or 8-ounce glass bottles containing 2 or 4 grams of didanosine respectively, and is to be mixed with commercial antacid before oral ingestion.

With particular emphasis on the tablets, whether ingested alone or as part of a combination ("cocktail") therapy regimen, the current chewable/dispersible buffered tablets are not conducive from a patient ease of use standpoint. Whereas the other products which are a part of the AIDS therapeutic cocktail are capsules or tablets and easily swallowed, the ddI Chewable/Dispersible Buffered Tablets must be thoroughly chewed or uniformly dispersed in water before administration.

Because ddI degrades rapidly at acidic pH, ddI, in its chewable/dispersible form and its buffered powder for oral solution form, contains buffering agents and is administered with antacids in the pediatric powder form. However, the presence of the large quantities of antacid components in the formulation can lead to significant GI imbalance as noted by severe diarrhea. Many patients also complain about chewing the large ddI tablets (a single dose is two tablets of 2.1 g each), the taste of the ddI or the time required to disperse the tablets and the volume of fluid (4 oz) required for the dose. As the current adult dose is 200 mg ddI, twice a day, or a single dose of 400 mg ddI daily, a high ddI load formulation without antacid or buffers is necessary to avoid the discomforting side effects and difficulty of administering the current ddI compositions.

SUMMARY OF THE INVENTION

The present invention relates to a spheronized beadlet comprising about 80% to about 100% by weight of an acid labile medicament, about 0% to about 10% by weight of a disintegrant, and about 0% to about 10% by weight of a binder selected from the group consisting of sodium carboxymethylcellulose, hydroxypropylmethylcellulose, potassium alginate, sodium alginate and partially pregelatinized corn starch. The present invention also relates to a high drug load pharmaceutical composition comprising said acid labile spheronized beadlet and an enteric coating disposed thereon. The present invention further relates to processes for making said spheronized beadlet and high drug load pharmaceutical composition.

The beadlets and pharmaceutical composition of the present invention are useful for administering a high loading of acid labile medicament is a small total amount of pharmaceutical composition.

DETAILED DESCRIPTION

In the present invention, a spheronized beadlet is provided wherein the beadlet contains (a) a high loading, about 80–100% by weight, of an acid labile medicament such as ddI, pravastatin, erythromycin, digoxin, pancreatin, 2',3'-dideoxyadenosine, 2',3'-dideoxycytosine and the like, (b) optionally one or more binders, and (c) optionally a disintegrant. Preferably, the acid labile medicament is ddI.

Binders, suitable for the present invention, are those which are non-acidic and, when utilized in small proportions, support formation of beadlets during spheronization. A suitable binder should also be non-acidic, and preferably alkaline, so as to minimize degradation of the acid labile medicament during spheronization. Typically, suitable binders include one or more binders wherein the amount of binder present in the core is an amount within the range of from about 0% to about 10% by weight, and preferably, about 1% by weight of the beadlet. In the present invention, sodium carboxymethylcellulose is the preferred binder. Examples of other binders, which are suitable for use in the present invention, include partially pregelatinized corn starch (Starch 1500; Colorcon, Ltd.), hydroxypropyl methylcellulose (HPMC) (Shin-Etsu Chemical Co., Ltd.), potassium alginate and sodium alginate.

The spheronized beadlet of the present invention may also include one or more disintegrants in an amount within the range from about 1% to about 4% by weight of the beadlet. Examples of suitable disintegrants include sodium starch glycolate (EXPLOTAB®; Edward Mendell Co.), crosslinked sodium carboxymethylcellulose (Ac-Di-Sol; FMC Corp), corn starch, and cross-linked polyvinylpyrrolidone. Sodium starch glycolate is the preferred disintegrant.

In the process of the present invention of high (80–100%) potency beadlets, containing acid labile medicaments, such as ddI, are formed using an aqueous extrusion/spheronization methodology. No specialized equipment is required as conventional extrusion and spheronization equipment was found to be adequate for beadlet formation. Use of a non-acidic, and preferably alkaline binder, such as sodium carboxymethylcellulose, and dusting during spheronization with a dry blend mixture, comprising the medicament, the optional binder, and the optional disintegrant, provide assurance of the chemical stability of the medicament and maximize the drug load. The process of the present invention also resulted in a high (>90%) yield of beads of narrow particle size cut.

The beadlets of the present invention may be prepared as follows. A granulation solvent, such as is typically suitable for spheronization of an acid labile medicament, is mixed with (a) an acid labile medicament, (b) optionally a binder, and (c) optionally a disintegrant, to form a wet mass. The preferred granulation solvent is water The relative proportions of the components in the wet mass are typically about 80–100 parts by weight acid labile medicament, about 0 to about 10 parts binder, about 0 to about 10 parts disintegrant, and about 20 to about 36 parts granulation solvent. Preferably, the relative proportions of the components of the wet mass containing ddI are about 95 parts ddI, 1 part sodium carboxymethylcellulose, 4 parts sodium starch glycolate and about 25 parts water.

The wet mass is then extruded, for example by employing a Nica or other type extruder, to form an extrudate. The extrudate is subsequently spheronized using a spheronizer such as Caleva, Nica or other type, to form beadlets. During spheronization, a dry mixture containing the same proportions of acid labile medicament, optional binder and optional disintegrant, as are present in the wet mass, is dusted onto the extrudate and onto the forming beadlets to absorb granulation solvent at the surface of the extrudate and beadlets and, thus, reduce the surface tackiness of the beadlets, thereby forming non-agglomerating beadlets.

In one embodiment, the dry mixture is prepared and then separated into two parts. Of these parts, a first part, containing about 4% to about 15% of the dry mixture, is set aside for use in dusting during spheronization, while the second part is mixed with the granulation solvent to form the wet mass which is subsequently extruded and spheronized.

Normally, drug beads are formed, through spheronization, by first preparing a wet mass which is extruded into threads or noodles. These threads or noodles are then spun on a high-speed rotating plate which breaks them into small pieces and rounds the ends to make spherical particles by a process known as spheronization. This spheronization generates centrifugal force. Under these forces, if the particles do not have enough moisture absorbent, the moisture will be extracted out of the particles (drawn to the surface during spheronization), which will cause agglomeration. Typically, in the art, microcrystalline cellulose, which is a good moisture absorbent, is used as the binder to support bead formation through spheronization. However, to adequately support formation of non-agglomerating beads during spheronization, microcyrstalline cellulose usually constitutes more than 15% by weight to about 30% by weight of the extrudate.

In the process of the present invention, non-agglomerating beadlets are formed by spheronization wherein the beadlets have a high drug loading (80–100% by weight) and a low binder loading (0–10% by weight). This is done (a) by using a medicament, optional binder, optional disintegrant mixture wherein the medicament itself, the medicament/ binder mixture, or the medicament/binder/disintegrant mixture is capable of becoming tacky upon wetting with a suitable granulation solvent to support beadlet formation, and (b) by dusting the beadlets, while forming during spheronization, with the dry mixture of the medicament, optional binder and optional disintegrant. During this process, moisture is extracted out of these particles. The dry mixture is dusted upon the moist particles to quench the surface moisture. This renders the particles relatively dry and free to move in a conventional rope formation pattern in the spheronizer. Accordingly, formulation of the beadlets by spheronization progresses without beadlet agglomeration.

Optionally, the non-agglomerating beadlets are then sized through mesh screens to obtain the desired beadlet sizes.

The non-agglomerating beadlets are then dried by suitable methods, such as by tray drying or by fluid bed drying, to form the dry spheronized beadlets of the present invention.

A pharmaceutical composition of the present invention comprises a core, which is the dry spheronized beadlet, and an enteric coating surrounding said core. Typically, the core employed in the pharmaceutical composition of the present invention may be formed of a beadlet or pellet having a diameter of from about 0.5 to about 5 mm, and preferably from about 1 to about 2 mm.

The enteric coating should provide for protection of the acid labile medicament at a pH less than 3 (such as found in the stomach) but will permit drug release at a pH of 4.5 or higher (such as found in the upper intestines).

As used herein "enteric coating", comprises a polymeric material, or materials, which encases the medicament core. A suitable enteric coating, of the present invention, is one which will have no significant dissolution at pH levels below 4.5.

Further, to provide a predictable dissolution profile, corresponding to the small intestine transit time of about 3 hours, and permit reproducible release therein, it is preferred that the enteric coating should begin to dissolve at a pH between about 4.5 and 5.5, which is within the pH range of the duodenum, and continue to dissolve at the pH range within the small intestine which is up to about 7.2 pH. Thus, the amount of enteric coating used should be such that it is substantially dissolved during the approximate three hour transit time within the small intestine.

Enteric coatings, suitable for the present invention, include enteric coating polymers known in the art, for example, hydroxypropyl methylcellulose phthalate (HP-MCP-HP50, USP/NF 220824 HPMCP-HP55, USP/NF type 200731 and HP55S; Shin Etsu Chemical), polyvinyl acetate phthalate (Coateric™; Colorcon Ltd.), polyvinyl acetate phthalate (Sureteric™; Colorcon, Ltd.), and cellulose acetate phthalate (Aquateric™; FMC Corp.) and the like.

Preferably, the enteric coating will use a methacrylic acid copolymer. More preferably, the methacrylic acid copolymer will be an aqueous acrylic resin dispersion. Even more preferably, the enteric coating will use an anionic copolymer derived from methacrylic acid and ethyl acrylate with a ratio of free carboxyl groups to the ester of approximately 1:1, having a mean molecular weight of approximately 250,000, which is supplied as in aqueous dispersion containing 30% w/w of dry lacquer substance, (Eudragit® L30D-55; Rohm-Pharma Co., Germany).

Most enteric coating materials known in the art are acidic in nature and may cause chemical degradation of an acid labile medicament when in direct contact with said medicament. This is especially true under the high temperature and humidity conditions experienced during an aqueous enteric coating process. To minimize this acid-caused degradation, a protective coat or subcoat is typically applied to the particles, beadlets, pellets, etc. prior to applying an enteric coating. This protective coat physically separates the acid labile medicament from the enteric coating thereby improving the stability of the medicament. Thus, in the present invention, it is most preferred that the enteric coating polymer will have a pH which does not cause significant degradation of the acid labile medicament within the core, typically a pH of about 4.5 or higher and preferably a pH of about 5.0 or higher.

When using an acidic enteric coating polymer in this process, the pH of said enteric coating polymer is raised by using a suitable alkalizing agent such as, for example, sodium hydroxide. The pH of the enteric coating polymer is raised to a point which is below the pH wherein the enteric integrity of the polymer could be lost. This partial acid neutralization provides a more stable composition for the acid labile drug in the core. As a result, there is no significant incompatibility between the acid labile medicament and the enteric coating. Thus, a protective subcoat between the medicament and the enteric coating is not necessary to reduce acid degradation of the core. This process also may allow for the quicker release of the medicament since a subcoat layer would delay drug release and since the pH of the enteric coating will only have to be slightly raised to result in the breakdown of the enteric coating.

In addition, the enteric coating will preferably contain a plasticizer. Examples of suitable plasticizers include triethyl citrate (Citroflex-2), triacetin, tributyl sebecate and polyethylene glycol.

Preferably, the plasticizer will be diethyl phthalate.

In the present invention, the enteric coating will have a weight ratio to the core within the range of from about 5% to about 30% to provide for release in the small intestine, but may be increased to approximately 60% for release in the colon.

More preferably, the enteric coating will include methacrylic acid copolymer in an amount of approximately 5–30%, and preferably 10%–20% by weight based on solids content of the enteric coating solution, and plasticizer in an amount of approximately 1%–6%, and preferably 2%–3% by weight. All of the above weights are based on total concentration of solids in the enteric coating solution/suspension.

The dry spheronized beadlets may then be coated with an enteric film coating suspension comprising the enteric coating polymer and optional plasticizer, using a suitable coating system such as a fluid bed coater or other suitable coating system, and then dried. It is preferred that during preparation of the film coating suspension, a NaOH solution is added to the suspension until a suitable pH is obtained Preferably, the pharmaceutical composition of the present invention further comprises an anti-adherent coating disposed on the exterior of the enteric coating. Often, enteric-coated or modified release beads or particles are prepared for oral delivery of the drugs in capsule dosage form. Upon oral ingestion the capsule shell dissolves allowing the contents in the capsule to be exposed to the gastric contents. Due to the presence of fluids in the stomach, exposed particles become moistened. If the moist particles do not stick together, they will disperse into the gastric contents and may begin to enter the duodenum based on the size distribution and other factors which control the gastric transit time. However, if the particles become tacky upon moistening, they may stick together as one or more lumps. In this case, such lumps may behave as large particles and their gastric emptying time will be variable depending upon the size and the strength of the lumps formed. In this case, such a dosage form would not behave as a true multiparticulate system. In order to reduce the potential for this problem, according to the process of the present invention, enteric-coated beadlets, pellets, particles or tablets are coated with a hydrophobic material before encapsulation. The amount of hydrophobic coating is kept to a level where it is just enough to prevent particle sticking after the capsule shell has dissolved, but not too much to retard dissolution. By this simple process, the particles behave as individual particles, and the gastric transit time is closer to that which is expected for the particle size for which the dosage form was designed, thus resulting in a more predictable and less variable dosage form.

The anti-adherent (anti-agglomerant) is typically a hydrophobic material such as talc, magnesium stearate or fumed silica. Talc is the preferred anti-adherent.

The invention is particularly adapted to pharmaceutical compositions such as beadlets, pellets or tablets, preferably beadlets, containing ddI as the medicament. ddI will be present in an amount of about up to 100% of the composition in the uncoated beadlets.

The beadlets may then be filled into hard shell capsules, such as gelatin capsules of varying sizes depending on the dosage of medicament desired.

It is preferred that the acid labile medicament be encapsulated within a capsule, or capsules, in a dose amount suitable for once daily or twice daily administration. For administration of ddI, the once daily dosage amount is about 400 mg of ddI while the twice daily dosage amount is about 200 mg ddI per dose.

A preferred enteric coated beadlet formulation is set out below.

| Material | Proportion Ranges | Preferred Proportion |
|---|---|---|
| CORE COMPONENT | | |
| Medicament | 80–100.00 | 95.00 |
| Binder | 0–10 | 1.00 |
| Disintegrant | 0–10 | 4.00 |
| ENTERIC COATING | | |
| Polymer | 5.0–30.0 | 10–20 |
| Plasticizer | 0.5–6.0 | 1.5–3.0 |
| ANTI-ADHERENT COATING | | |
| Anti-adherent | 0.1–4.0 | 0.2–0.5 |

The Example represents a preferred embodiment of the present invention. The following example further describes the materials and methods used in carrying out the invention and is intended to be for illustrative purposes only, and is not intended to limit the scope or spirit of this invention or the claims in any way. All temperatures are expressed in degrees Centigrade unless otherwise indicated and all mesh sizes are U.S. standard ASTM.

EXAMPLE

A preferred ddI formulation in the form of enteric coated beadlets was prepared as described below. ddI (60 kg), sodium starch glycolate (2.523 kg) and NaCMC (0.633 kg) were placed in a PMA 300 mixer and then were mixed for 5±2 min at 200 RPM to form a dry blend. Prior to mixing, if any of the ingredients required delumping, they were passed through a #20 mesh stainless steel screen.

Approximately 4–15% of the dry blend, preferably 9.5%, was then removed and set aside for use in dusting during spheronization. The remaining dry blend was then granulated by adding 16 kg of 20–40° C. water while mixing at 200 RPM until a suitable wet mass was achieved for extrusion. The wet mass was extruded through a suitable screen using a Nica Model E140, Feeder Speed 1, Agitator Speed 1 extruder The extrudate was then transferred to a spheronizer system, fitted with a 1.25 mm screen and radial cross hatch friction plates, and spheronized at 300 RPM for approximately 1.5 minutes to form wet beadlets. During spheronization, the dry blend, which was previously set aside, was used to dust the wet beadlets to prevent beadlet agglomeration. After the appropriate spheronization time, the product was discharged.

The spheronized wet beadlets were then gently passed through #10 and #18 size mesh screens to collect 10/18 mesh product fraction. The over 10 and under 18 sized mesh fractions were returned to the extruder for re-extrusion and spheronization. This process was continued until at least 90% of the product fraction was obtained. The 10/18 mesh product fraction was then dried using a Glatt GPCG120 fluid bed dryer set at 65° C. to achieve a moisture content of less than 3%. The dried beadlets were then screened through #10 and #20 mesh screens to remove any lumps or undersized beadlets. The 10/20 mesh product fraction dried beadlets were collected.

To prepare sufficient quantities of film coating to coat 140 kg of dried beadlets, Eudragit L-30-D 55 was filtered through a #60 mesh screen to remove any lumps present therein and then the Eudragit (101.5 kg, dry weight) was mixed with 43 kg of water The mixture was continuously stirred for 15 minutes. Subsequently, with continued stirring, at 20–35° C. NaOH solution (0.15 kg NaOH, 3.75 kg water) was added to the vessel until a pH of 5.0±0.1 was obtained. Subsequently, with continuous stirring, diethyl phthalate (4.566 kg) was added to the vessel. Stirring continued for an additional 20 minutes.

The beadlets were then coated with 1.09 kg of coating suspension per kg of beadlets, using a GLATT GPCG-120 with a 32" Wurster Coater, to achieve a 16–20% w/w film coating.

Before commencing application of the film coating suspension, the beadlets were charged into the column of the GPCG-120, fluidized with an air flow of 1900–2400 CFM, and then heated to approximately 40° C. The coating suspension was then sprayed onto these fluidized beadlets while adjusting air flow or coating suspension flow to maintain temperature between 32–37° C. After coating, beadlet fluidization was continued for 15 minutes to permit beadlet cooling.

The weight of the talc, about 0.002 kg of talc per kg of coated beads, to add based on the net weight of the coated beadlets was determined. The enterically coated beadlets were then placed in a suitable tumbling type blender with the talc and blended for 15±5 minutes. The beadlets were then transferred to a suitable container(s) lined with two polyethylene bags and the net weight was determined.

The so formed beadlets may then be filled in to capsules or shells, such as gelatin capsules for ease of swallowing.

The so formed enteric coated ddI product was found to give excellent protection against gastric acid (at pH of 3) but had excellent release of ddI at pH's above 4.5.

The invention claimed is:

1. A pharmaceutical composition comprising a core in the form of a beadlet, an enteric coating for said core, and an anti-adherent coating disposed on the exterior of said enteric coating, said core comprising about 80% to about 100% by weight of an acid labile medicament which is 2',3'-dideoxyinosine, about 0% to about 10% by weight of a disintegrant, and about 0% to about 10% by weight of a binder selected from the group consisting of sodium carboxymethyl cellulose, hydroxypropylmethyl cellulose, potassium alginate, sodium alginate and partially pregelatinized corn starch, said composition being devoid of a protective coat or subcoat between the core and the enteric coating, wherein the weight ratio of enteric coating to core is between about 0.0:5:1 to about 0.6:1, and wherein the enteric coating should provide protection of the medicament at a pH less than 3 but will permit drug release at a pH of 4.5 or higher, said enteric coating comprising a polymer which is selected from the group consisting of polyvinyl acetate phthalate, cellulose acetate phthalate and a methacrylic acid copolymer.

2. The pharmaceutical composition of claim 1 wherein said enteric coating comprises a polymer and a plasticizer.

3. The pharmaceutical composition of claim 2 wherein said polymer is selected from the group consisting of polyvinyl acetate phthalate and cellulose acetate phthalate.

4. The pharmaceutical composition of claim 2 wherein said polymer comprises a methacrylic acid copolymer.

5. The pharmaceutical composition of claim 4 wherein said enteric coating includes the methacrylic acid copolymer in an amount within the range of from about 5 to about 30% of the total composition weight, and said plasticizer in an amount within the range from about 0.5 to about 6% of the total composition weight.

6. The pharmaceutical composition of claim 4 wherein said methacrylic acid copolymer is a copolymer of methacrylic acid and ethyl acrylate.

7. The pharmaceutical composition of claim 2 wherein said plasticizer is triethyl citrate, triacetin, tributyl sebecate, or polyethylene glycol.

8. The pharmaceutical composition of claim 2 wherein said plasticizer is diethyl phthalate.

9. The pharmaceutical composition of claim 2 wherein said enteric coating includes methacrylic acid copolymer and diethyl phthalate.

10. The pharmaceutical composition of claim 1 wherein the anti-adherent coating is magnesium stearate or fumed silica or talc.

11. The pharmaceutical composition of claim 10 further comprising an anti-adherent coating disposed on the exterior of said enteric coating.

12. The pharmaceutical composition of claim 10 wherein said anti-adherent is present in an amount within the range from about 0.1% to about 4.0% of the total composition weight.

13. The pharmaceutical composition of claim 1 wherein said disintegrant is cross-linked sodium carboxymethylcellulose, corn starch, or cross linked polyvinylpyrrolidone.

14. The pharmaceutical composition of claim 1 wherein said disintegrant is sodium starch glycolate.

15. The pharmaceutical composition of claim 1 wherein said binder is alkaline.

16. The pharmaceutical composition of claim 15 wherein said binder is sodium carboxymethylcellulose.

17. A pharmaceutical composition comprising a core in the form of a beadlet, an enteric coating for said core, and an anti-adherent coating disposed on the exterior of said enteric coating, wherein said core comprises about 95% by weight 2',3'-dideoxyinosine, and about 1% by weight sodium carboxymethylcellulose and about 4% by weight sodium starch glycolate and said enteric coating comprising a copolymer of methacrylic acid and ethyl acrylate, where said composition being devoid of a protective subcoat between the core and the enteric coating.

18. The pharmaceutical composition of claim 1 wherein said composition is encapsulated in a capsule for oral administration.

19. The pharmaceutical composition of claim 18 wherein said capsule is filled with said composition in an amount equivalent to attain a dosage of 2′,3′-dideoxyinosine required for twice daily administration.

20. The pharmaceutical composition of claim 18 wherein said capsule is filled with said composition in an amount equivalent to attain a dosage of 2′,3′-dideoxyinosine required for once daily administration.

21. A pharmaceutical composition comprising:
    a) a dissolvable capsule; and
    b) the pharmaceutical composition of claims 1,11, or 17 which is encapsulated within said dissolvable capsule.

22. The pharmaceutical composition of claim 1 wherein the enteric coating includes an alkalizing agent.

23. The pharmaceutical composition of claim 17 wherein the enteric coating includes an alkalizing agent.

* * * * *

UNITED STATES PATENT AND TRADEMARK OFFICE
CERTIFICATE OF CORRECTION

PATENT NO. : 7,122,207 B2  Page 1 of 1
APPLICATION NO. : 09/848448
DATED : October 17, 2006
INVENTOR(S) : Ismat Ullah et al.

It is certified that error appears in the above-identified patent and that said Letters Patent is hereby corrected as shown below:

Title Page:

Item (63), line 5 thereof: "No. 09/083,579" should read -- No. 09/083,597 --.

Column 8, line 6, "celiulose" should read -- cellulose --.

Signed and Sealed this

Fourteenth Day of August, 2007

JON W. DUDAS
*Director of the United States Patent and Trademark Office*

UNITED STATES PATENT AND TRADEMARK OFFICE
CERTIFICATE OF CORRECTION

PATENT NO.        : 7,122,207 B2                                  Page 1 of 1
APPLICATION NO.   : 09/848448
DATED             : October 17, 2006
INVENTOR(S)       : Ullah et al.

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by (446) days Delete the phrase "by 446" and insert -- by 377 days--

Signed and Sealed this

Sixteenth Day of October, 2007

JON W. DUDAS
*Director of the United States Patent and Trademark Office*